US009228962B2

(12) United States Patent
Kociak et al.

(10) Patent No.: US 9,228,962 B2
(45) Date of Patent: Jan. 5, 2016

(54) ADJUSTABLE CATHODOLUMINESCENCE DETECTION SYSTEM AND MICROSCOPE EMPLOYING SUCH A SYSTEM

(71) Applicants: CENTRE NATIONAL DE LA RECHERCHE SCIENTIFIQUE, Paris (FR); UNIVERSITE PARIS SUD 11, Orsay (FR)

(72) Inventors: Mathieu Kociak, Palaiseau (FR); Luiz Fernando Zagonel, Campanas (BR); Marcel Tence, Issy les Moulineaux (FR); Stefano Mazzucco, Bethesda, MD (US)

(73) Assignees: Centre National de la Recherche, Paris (FR); Universite Paris Sud 11, Orsay (FR)

( * ) Notice: Subject to any disclaimer, the term of this patent is extended or adjusted under 35 U.S.C. 154(b) by 0 days.

(21) Appl. No.: 14/540,220

(22) Filed: Nov. 13, 2014

(65) Prior Publication Data

US 2015/0076364 A1 Mar. 19, 2015

Related U.S. Application Data

(63) Continuation of application No. 13/699,981, filed as application No. PCT/FR2011/050987 on Apr. 29, 2011, now Pat. No. 8,912,509.

(30) Foreign Application Priority Data

May 27, 2010 (FR) ...................................... 10 54108

(51) Int. Cl.
*G01N 21/64* (2006.01)
*G01N 23/225* (2006.01)
(Continued)

(52) U.S. Cl.
CPC .......... *G01N 23/2254* (2013.01); *H01J 37/228* (2013.01); *H01J 37/244* (2013.01);
(Continued)

(58) Field of Classification Search
CPC . H01J 37/228; H01J 2237/2482; H01J 37/28; G01N 23/2254
USPC ...................................................... 250/458.1
See application file for complete search history.

(56) References Cited

U.S. PATENT DOCUMENTS 3,845,305 A 10/1974 Liebl
5,013,915 A 5/1991 Isakozawa et al.
(Continued)

FOREIGN PATENT DOCUMENTS

EP 1956632 8/2008
JP 2003157789 5/2003

OTHER PUBLICATIONS

Watabane et al., "Spatial resolution of imaging contaminations on the GaAs surface by scanning tunneling microscope—cathodoluminescence spectroscopy," 2008, Applied Surface Science, vol. 254, pp. 7737-7741.*

*Primary Examiner* — Kiho Kim
(74) *Attorney, Agent, or Firm* — Greer, Burns & Crain, Ltd.

(57) ABSTRACT

A cathodoluminescence detection system is provided, including
  a source of charged particles arranged to illuminate a sample with a charged particle beam, and
  an optical path having at least two optical components capable of collecting and conveying light radiation coming from the illuminated sample to an analysis device;
  each optical component of the optical path is selected so that:
  the maximum output angle of the optical component is less than or equal to 120% of the maximum acceptance angle of the next optical component; and
  the diameter of the radiation coming from the optical component in the input plane of the next optical component is less than or equal to 120% of the useful input diameter of the next optical component.

15 Claims, 7 Drawing Sheets

(51) Int. Cl.
*H01J 37/22* (2006.01)
*H01J 37/244* (2006.01)
*H01J 37/28* (2006.01)
*H01J 37/26* (2006.01)

(52) U.S. Cl.
CPC .............. *H01J 37/261* (2013.01); *H01J 37/28* (2013.01); *G01N 2201/08* (2013.01); *H01J 2237/024* (2013.01); *H01J 2237/063* (2013.01); *H01J 2237/2448* (2013.01); *H01J 2237/24475* (2013.01); *H01J 2237/24485* (2013.01); *H01J 2237/2602* (2013.01); *H01J 2237/2802* (2013.01); *H01J 2237/2808* (2013.01)

(56) References Cited

U.S. PATENT DOCUMENTS

| | | | |
|---|---|---|---|
| 5,194,912 | A | 3/1993 | Batchelder |
| 6,476,387 | B1 | 11/2002 | Nishimura et al. |
| 7,589,322 | B2 | 9/2009 | Nishikata et al. |
| 2003/0053048 | A1 | 3/2003 | Bennett |
| 2007/0023655 | A1 | 2/2007 | Nishikata et al. |
| 2007/0112529 | A1* | 5/2007 | Bigarre et al. .................. 702/59 |
| 2008/0185509 | A1* | 8/2008 | Knowles ....................... 250/251 |
| 2008/0315093 | A1 | 12/2008 | Hasegawa |

* cited by examiner

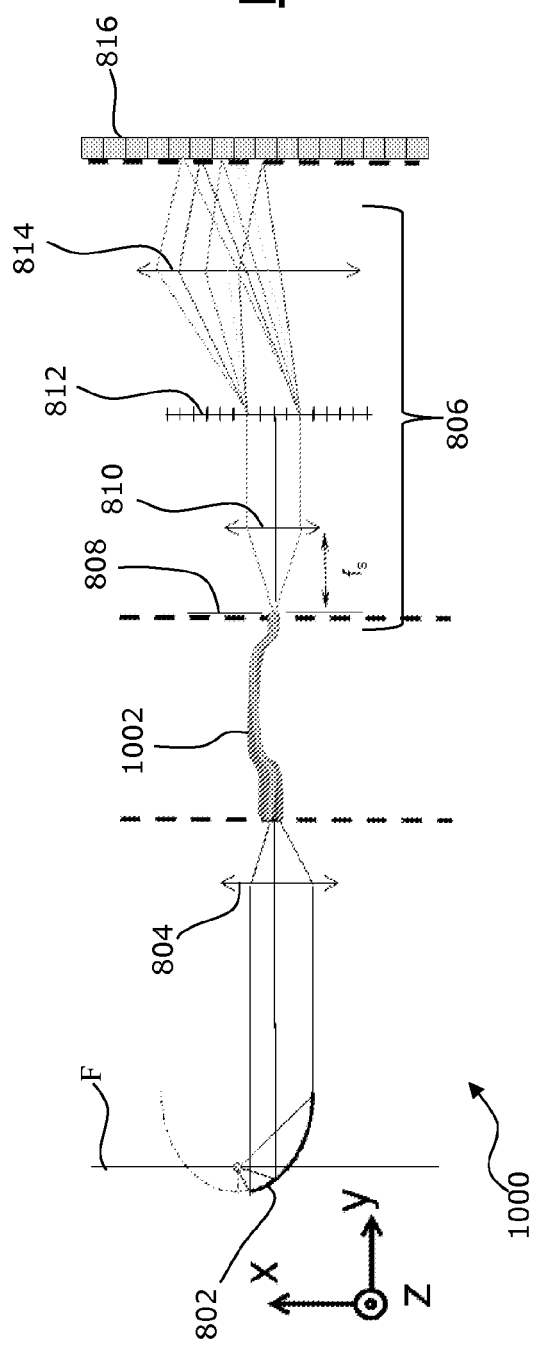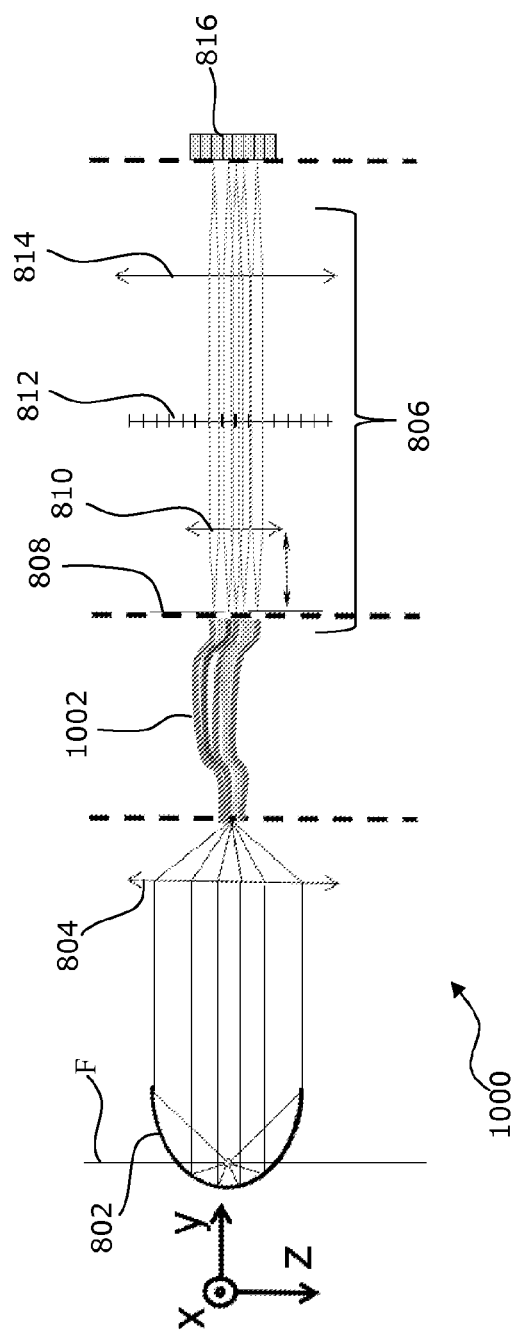

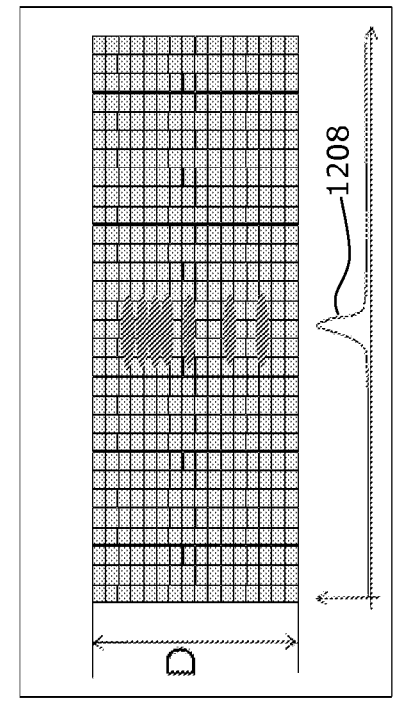
FIG.12
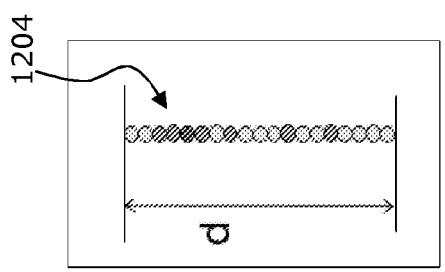
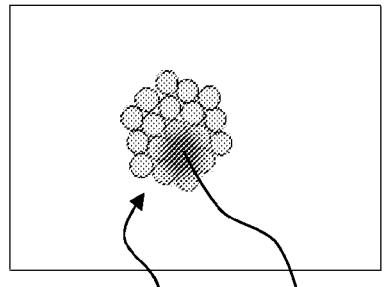
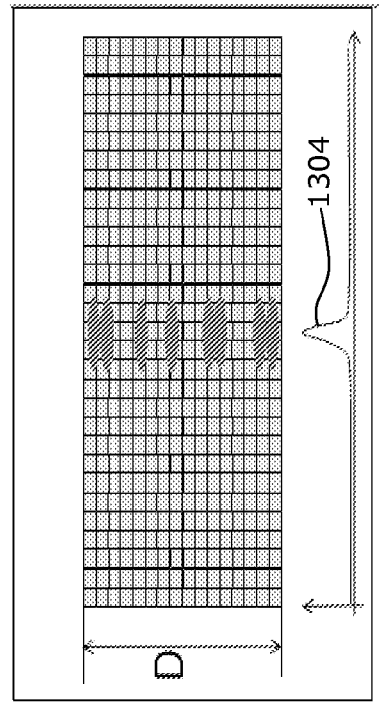
FIG.13
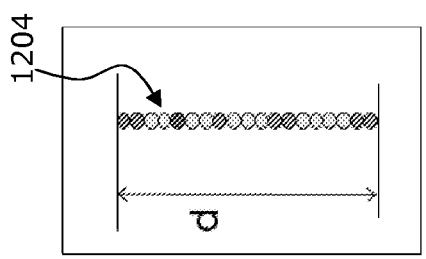
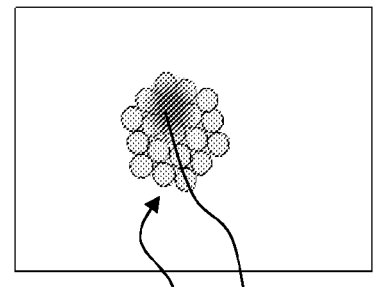

ADJUSTABLE CATHODOLUMINESCENCE DETECTION SYSTEM AND MICROSCOPE EMPLOYING SUCH A SYSTEM

RELATED APPLICATION

The present application claims priority pursuant to 35 USC 120 from U.S. patent application Ser. No. 13/699,981 filed Nov. 26, 2012.

BACKGROUND

The present invention relates to a cathodoluminescence detection system. It also relates to a microscope implementing such a system.

The field of the invention is the field of cathodoluminescence, and more particularly the field of systems using charged particles such as charged particle microscopes, for example microscopes using the principle of cathodoluminescence.

Numerous cathodoluminescence detection systems coupled with charged particle microscopes are currently known, such as transmission electron microscopes (TEM) and scanning transmission electron microscopes (STEM).

The physical effect used in these microscopes, known as cathodoluminescence, is based on the detection of optical signals emitted due to excitation by a charged particle beam. The microscopes used are equipped with a charged particle cannon producing a charged particle beam that is aimed at a sample under examination. The sample struck by the particle beam is excited and in turn emits light radiation. The light radiation is collected by a collection optic the role of which is to direct the light radiation towards means of analysing said light radiation. So-called adjustment means can be arranged between the collection optic and the analysis means to modify and convey the light radiation to the input of the analysis means. Such a microscope is described in U.S. Pat. No. 7,589,322. The collection optic is located in a vacuum chamber of the microscope.

However, the known cathodoluminescence detection systems are not flexible. These microscopes and the cathodoluminescence detection systems that they implement do not allow for optimised light radiation collection combined with conservation of intensity and radiance (power per unit solid angle per unit area) along the light path to the analysis means. In particular, they do not allow for optimum collection of the optical signal combined with optimum spectral resolution.

An aim of the present invention is to remedy the aforementioned drawbacks.

Another aim of the present invention is to propose a cathodoluminescence detection system that improves the collection of the light radiation.

Moreover, a further aim of the invention is to propose a cathodoluminescence detection system that conserves both the intensity and radiance of the signal collected over the entire light radiation path.

SUMMARY

According to an aspect of the invention, at least one of these aims is achieved by a cathodoluminescence detection system comprising a collection optic collecting light radiation coming from a sample illuminated by a charged particle beam and sending said light radiation to analysis means, characterised in that it comprises means of positioning said collection optic in at least one dimension.

In this application, the terms "upstream" and "downstream" are defined relative to and in the direction of the light radiation path, i.e., in the direction from the charged particle emission source towards the sample, then towards the collection optic and finally towards the light radiation analysis means.

The collection optic is defined as being all of the components performing the collection of the light radiation emanating from the sample and sending this light radiation towards the analysis means.

The system according to the invention comprises means of positioning the collection optic in at least one dimension. The system according to the invention thus allows for the spectral resolution and the intensity of the radiation to be conserved over the entire path.

Firstly, the system according to the invention allows for the collection optic to be positioned relative to the charged particle beam emission source without modifying the flow of charged particles.

Secondly, the system according to the invention allows each user to optimise the positioning of the collection optic in such a way as to obtain the position allowing for the most light radiation emanating from the sample under examination to be collected.

Finally, by providing the option of repositioning the collection optic, the system according to the invention allows each user to position the collection optic in such a way as to ensure on the one hand that the intensity of the light radiation collected by the collection optic is conserved up to the analysis means and on the other hand that the collection optic or the optic after the collection optic allows for the formation of a spot of a size ultimately restricted by the laws of geometric optics and diffraction, from the radiation emitted.

Advantageously, the collection optic positioning means can comprise means of translating said collection optic in at least one dimension.

The collection optic positioning means can also comprise means of rotating said collection optic about at least one rotation axis.

Advantageously, the positioning means can comprise at least one positioning component, for example a micrometer screw, a piezoelectric actuator or a capacitive actuator, each positioning component being capable of moving said collection optic directly or indirectly in at least one dimension.

Thus, the positioning means, respectively the rotation means, can enable a user to improve the positioning of the collection optic in the three dimensions of space, respectively on the three Euler angles.

In a particular embodiment, the collection optic can comprise a parabolic mirror sending the light radiation, for example in a collimated manner. In this case, the parabolic mirror can comprise a through-hole arranged opposite the charged particle emission source and letting the charged particle beam through to the sample.

In a second particular embodiment, the collection optic can comprise a plane mirror. This plane mirror can be combined with a collecting lens arranged downstream of said plane mirror and sending the light radiation, for example in a collimated manner. In this case, the plane mirror can comprise a through-hole arranged opposite the charged particle emission source and letting the charged particle beam through to the sample.

In a third particular embodiment, the collection optic can comprise an elliptical mirror, possibly combined with a collecting lens arranged downstream of the elliptical mirror. In this case, the elliptical mirror can comprise a through-hole arranged opposite the charged particle emission source and letting the charged particle beam through to the sample.

More generally, the collection optic can comprise a concave mirror.

Advantageously, the positioning means comprise a stage that can be moved in at least one dimension and the collection optic is integral/stands with said stage. Thus, by modifying the position of the stage, the position of the collection optic can be modified.

The stage can either be arranged in the vacuum chamber of a microscope, and positionable from inside or outside, or more advantageously arranged outside the chamber and positionable from outside the chamber.

The stage can also be located outside the vacuum chamber. In this case, the collection optic can be securely connected to the stage using connection means such as one or more screws or a tube passing through the wall of the vacuum chamber in a manner that is both leaktight and allows for free movement in one or more dimensions of space. Such a leaktight connection that allows for free movement can for example be achieved by means of a bellows seal fixed to part of the wall of the microscope vacuum chamber. Such a bellows seal conserves the leaktightness of the vacuum chamber while allowing for the movement of the screws or tube passing through it.

The micrometer screws can be arranged to allow for the movement of a stage securely connected to the collection optic.

In a particularly advantageous embodiment, the system according to the invention can comprise a cylindrical tube, called outer cylinder, for example a cylinder of revolution, centred relative to the axis of the collection optic, rigidly secured to said collection optic and mounted so that it can be moved by the positioning means, said collection optic being moved by moving said external tube. Thus, in this case, the movement of the outer cylinder results in the movement of the collection optic. Furthermore, as the outer cylinder is integral with the collection optic, the axis of the outer cylinder is aligned with the axis of the collection optic at all times, even when they are moved.

The collection optic can be mounted rigidly, for example by means of one or more screws, at the end of the outer cylinder on the side of the vacuum chamber in which the collection optic is located. This end will be referred to, in the rest of the description, as the proximal end. The other end of the cylinder, that is, the end of the cylinder on the side of the analysis means, will be referred to as the distal end of the cylinder.

In a particular embodiment, the outer cylinder can be securely mounted to a stage that can be moved in one or more dimensions, for example using micrometer screws. In this case, the micrometer screws are arranged to effect the movement of the stage assembly secured to the outer cylinder at the end of which the collection optic is secured.

The system according to the invention can also comprise a cylindrical tube, called inner cylinder, for example a cylinder of revolution, arranged centred in the outer cylinder and capable of receiving optical means of adjusting the light radiation with a view to injecting said light radiation directly into analysis means such as a photomultiplier, camera or spectrometer equipped with a camera or a photomultiplier or via an optical fibre to one of these analysis means. The optical adjustment means can comprise a set of lenses and/or mirrors allowing for the size of the optical radiation to be adjusted to the space constraints imposed by the walls of the tube in order to conserve the intensity up to the final detector. The various components of the adjustment optic will have numerical apertures adjusted relative to each other and relative to the detection systems or optical fibre, again to preserve the intensity along the optical radiation path. If an optical fibre is used before the detector, its diameter and numerical aperture will be adjusted to said detection system.

The optical fibre is capable of conveying the light radiation sent by the collection optic to the analysis means.

The inner cylinder can be mounted in the outer cylinder, rotating freely relative to said outer cylinder. It is thus possible to adjust the orientation of the optical components located in the inner cylinder.

The inner cylinder can comprise any optical component used for the needs of the experiment, for example a polariser.

The cathodoluminescence detection system according to the invention can also comprise means of analysing the light radiation collected by the collection optic.

The analysis means can comprise, in a non-exhaustive manner, a CCD camera and/or a photomultiplier, preceded or not by a spectrometer.

In a particular embodiment, the optical fibre is directly connected to the analysis means.

In a particular embodiment, the optical fibre can be replaced by a set of adjacent fibres directly connected to the analysis means.

In a particular embodiment, the adjacent fibres are arranged in a disc upstream, and in a line downstream. The disc arrangement allows for the signal to be collected even in the event of a slight offset, and the line arrangement allows for optimisation of the intensity and spectral resolution when the set of fibres is placed at the input of an optical spectrometer, for example.

The system according to the invention can comprise, downstream of the collection optic, means for the optical adjustment of the light radiation with a view to injecting said light radiation into an optical fibre or a detector, such as for example a lens allowing for the adjustment of the size of the light radiation and the angle of incidence at the input of an optical fibre or detector.

Advantageously, the adjustment means can comprise a diaphragm arranged to let the light radiation coming from the collection optic through to the analysis means and block at least one undesirable optical signal. In a particular embodiment, a diaphragm can be placed centred along the optical axis, allowing for the light radiation emitted around the focal point of the collection optic (on the sample) to be let through and allowing for the light radiation emitted from other areas of the sample to be filtered.

When the charged particle beam strikes the sample, it can eject different particles such as so-called secondary electrons and ions and so-called back scattered charged particles. These secondary and back scattered particles can in turn strike different objects inside the microscope (and far from the focal point of the collection optic) and cause the emission of irrelevant light radiation, which will thus be filtered with a diaphragm.

Advantageously, the adjacent fibres, arranged in a disc upstream, have a small diameter designed to act as a diaphragm.

The invention also allows for the proposal of a flexible, easy-to-maintain cathodoluminescence detection system. To this end, the invention proposes a cathodoluminescence detection system in which the collection optic is arranged in a chamber inside which the pressure is below atmospheric pressure, called vacuum chamber, and the adjustment means are arranged in an environment in which the pressure is greater than the pressure in said chamber, for example atmospheric pressure, said system also comprising sealing means arranged between said chamber and said adjustment means to maintain the pressure in said chamber.

In a particular embodiment of the cathodoluminescence detection system according to the invention, the collection optic is securely mounted at the proximal end of the outer cylinder, fully centred on and coaxial with the optical axis of the collection optic. The outer cylinder comprises, on the side of its proximal end, a transparent window seal arranged to preserve the leaktightness of the vacuum chamber. The inner cylinder is removably inserted into the outer cylinder and can optionally rotate freely. The inner cylinder is mounted coaxially with the outer cylinder and is therefore necessarily centred relative to the optical axis of the collection optic. The adjustment means, together with the input of the optical fibre, are arranged in the inner cylinder and are therefore at atmospheric pressure. These components can easily be accessed by an operator as the inner cylinder is removable. The inner cylinder can also comprise any optical component, such as for example a polariser.

The outer cylinder is surrounded by at least one sealing means permitting the movement of the outer cylinder in the three directions of space while preserving the leaktightness of the vacuum chamber in which the collection optic is located. Such sealing means can for example comprise a bellows seal permitting the movement of the cylinder in all three directions and mounted on a wall of the vacuum chamber around or level with an opening made in this wall in the direction followed by the light radiation sent by the collection optic to the analysis means.

The outer cylinder is securely mounted on a stage. This stage can be moved in the three directions of space by means of micrometer screws. Thus, by moving the stage, the operator can move the outer cylinder and the collection optic.

When the stage, outer cylinder and collection optic assembly is moved, the leaktightness of the vacuum chamber is conserved by means of the bellows seal surrounding the outer cylinder and secured to the wall of the vacuum chamber, and by means of the window seal arranged in the outer cylinder.

The collection optic is integral with the outer cylinder. The latter is centred relative to the optical axis of the collection optic. The inner cylinder is centred relative to the outer cylinder. All of the components located inside the inner cylinder are thus centred relative to the optical axis of the collection optic. As the collection optic+outer cylinder+inner cylinder are securely attached to each other, they remain fully centred at all times.

Advantageously, the components located in the inner cylinder are placed as close as possible to the collection optic to reduce the effects of any slight misalignment between the optical axis of the collection optic and the centre of the inner cylinder.

Advantageously, said outer cylinder has a sufficiently large inner diameter to allow for the use of optical components, such as lenses, or detectors such as photomultipliers and CCD cameras, inside the outer cylinder.

Advantageously, the collection optic can have a conductive surface electrically isolated from the rest of the device and the microscope. The collection optic can thus be placed at a low electric potential relative to the mass of the microscope, optionally via a wire accessible from the outside of the microscope via a sealed electrical passage, in order to thus detect any contact with the microscope through the appearance of an electric current. The collection optic is located in a crowded space and should not be knocked against the standard components of the microscope, such as the sample or the pole piece. These movements must be carefully monitored. By measuring the electric current between the collection optic and the microscope, it is possible to determine the occurrence of slight contact between the collection optic and the microscope.

Advantageously, the system according to the invention can also comprise an emission source of a light beam propagating in the opposite direction to the direction of propagation of the detected light radiation coming from the sample and received by the collection optic, said light beam being directed towards the sample by the collection optic.

The cathodoluminescence system can also be used to inject light onto the sample. In this case, the cathodoluminescence system comprises a light beam emission source instead of or as well as the detection system. This source is then arranged to emit a light beam in the opposite direction to the direction of propagation of the detected light radiation, i.e. from downstream to upstream. The light source is focused on the sample, the areas of exposure to the charged particles and the light beam thus being superimposed. The light source can be a spatially coherent light source, for example a laser, so that the size of the light beam striking the sample is only limited by the laws of geometric optics and diffraction in order to optimise the power density received by the sample.

Advantageously, the system according to the invention can also be used with a light radiation separator and can be used to inject light onto the sample and at the same time collect the light emitted by the sample.

The cathodoluminescence system can also be used to detect the light radiation emitted by the sample by the effect of photoluminescence, i.e. when a light beam strikes an object, which in turn incites it to emit light radiation. This separator is then arranged to allow for the injection of a light beam from downstream to upstream and the simultaneous detection of light radiation from upstream to downstream. The small size of the injected beam can allow for the excitation of a small part of the sample, which can at the same time be imaged with the charged particle beam of the microscope. The light radiation emitted by the sample during the injection of light can be analysed in the same way as the light radiation emitted following the interaction of charged particles.

According to another aspect of the invention, a cathodoluminescence system is proposed that allows for the collection of the light radiation coming from the sample illuminated by a beam of nanometric or sub-nanometric charged particles with which the surface of the sample is optionally scanned, and its conveyance to analysis means while conserving more light intensity and spectral resolution compared with the cathodoluminescence systems of the state of the art.

According to the invention, such a cathodoluminescence system comprises:
  a source of charged particles arranged to illuminate a sample with a charged particle beam, and
  an optical path comprising at least two optical components capable of collecting and conveying light radiation coming from said illuminated sample to analysis means;
said system being characterised in that each optical component of said optical path is selected so that:
  the maximum output angle of said optical component is less than or equal to 120% of the maximum acceptance angle of the next optical component; and
  the diameter of the radiation coming from said optical component in the input plane of the next optical component is less than or equal to 120% of the useful input diameter of the next optical component.

Thus, according to the invention each component transmits at least 60% of the optical signal. Just 20% of the optical signal is lost at each optical component on the optical path.

Such a cathodoluminescence system allows for the collection of the light radiation coming from the illuminated sample and its conveyance to the analysis means while conserving more light intensity compared with the cathodoluminescence systems of the state of the art.

According to a preferred embodiment of the system of the invention, each optical component on the optical path is selected so that the maximum output angle of an optical component is less than or equal to the maximum acceptance angle of the next optical component. Thus, the output angle of an optical component is adjusted and the light radiation leaving an optical component reaches the next optical component at such an angle that all of the light radiation enters the next optical component.

Still according to a preferred version of the system according to the invention, each optical component of the optical path is selected so that the diameter of the radiation coming from an optical component in the input plane of the next optical component is less than or equal to the useful input diameter of the next optical component. Thus, all of the light radiation reaching the next optical component enters the next optical component.

In a combination of these two preferred versions of the system according to the invention, this version being the preferred version of the invention, the optical signal is transmitted from one optical component to another without any loss of intensity other than that due to the absorption or diffusion of the optical systems and all of this intensity of the optical signal is conserved along the entire optical path.

Advantageously, when the optical path comprises N optical components, each optical component of the optical path can be positioned so that the offset of one optical component relative to the centre of the previous optical component complies with the following relationship:

$$Ds_i/2 \leq 1.2 De_{i+1}/2 - \Delta_{i+1} \text{ for } i=1 \ldots N-1$$

where:
$\Delta_{i+1}$ is the offset of optical component i+1 relative to the centre of optical component i,
$De_{i+1}$ is the useful input diameter of component i+1,
$Ds_i$ is the diameter of the radiation coming from component i measured at the input of component i+1.

Such a system allows for improved positioning relative to the systems of the state of the art and thus for conveyance of the light radiation along the entire optical path with little loss.

In a preferred version of the system according to the invention, each optical component of the optical path can be positioned so that the offset of one optical component relative to the centre of the previous optical component verifies the following equation:

$$Ds_i/2 \leq De_{i+1}/2 - \Delta_{i+1} \text{ for } i=1 \ldots N-1$$

where:
$\Delta_{i+1}$ is the offset of optical component i+1 relative to the centre of optical component i,
$De_{i+1}$ is the useful input diameter,
$Ds_i$ is the diameter of the beam coming from component i measured at the input of component i+1.

Such a system allows for positioning of the optical components such that all of the radiation leaving an optical component enters the next optical component without any loss other than that caused by absorption or diffusion as none of the optical components is offset relative to the previous optical component to such an extent that some of the radiation is lost.

According to the invention, one of the optical components on the optical path can be a spectrometer, and more particularly a spectrometer comprising a focusing component at its input.

In this case, the spectrometer and the other optical components of the optical path can be selected so that the width of the beam at the input of the spectrometer in the dispersive direction is less than or equal to 10 times the limit diameter at the input of the spectrometer below which the resolution of the spectrometer no longer depends on the diameter of the waist of the light radiation at the input of the spectrometer. The value of such a limit diameter is provided by the spectrometer manufacturer and depends largely on its magnification in the dispersive direction.

Thus, the system according to the invention allows for the light radiation to be conveyed to the spectrometer without any loss of intensity, as the diameters and angles are adjusted, while ensuring the optimum spectral resolution for a given spectrometer.

Still in a situation in which one of the components of the optical path is a spectrometer, the spectrometer and the other optical components of the optical path can preferably be selected so that the width of the beam at the input of the spectrometer in the dispersive direction is less than or equal to the limit diameter at the input of the spectrometer below which the resolution of the spectrometer no longer depends on the diameter of the waist of the light radiation at the input of the spectrometer.

Thus, the system according to the invention allows for the light radiation to be conveyed to the spectrometer without any loss of intensity, as the diameters and angles are adjusted, while ensuring optimum spectral resolution for a given spectrometer.

In a particular embodiment, the optical component before the spectrometer can comprise an optical fibre the output of which is positioned or imaged at the input of the spectrometer.

In this case, the optical fibre and the optical component before the optical fibre can be selected so that:
the diameter of the beam coming from the previous optical component measured at the input of the fibre is less than or equal to 120%, preferably less than or equal to 100%, of the useful diameter of the optical fibre, and
the maximum input angle of the beam coming from the previous optical component is less than or equal to 120%, preferably less than or equal to 100%, of the limit angle of incidence of said optical fibre.

Thus, the optical path is perfectly adjusted so that all of the light radiation enters the optical fibre under conditions such that all of the optical radiation is conveyed to the spectrometer without loss or with negligible loss.

In a particularly advantageous and preferred embodiment of the invention, the optical component before the spectrometer can comprise a plurality of optical fibres constituting an optical fibre bundle, the fibres of said bundle being aligned, on the side of said spectrometer, perpendicular to the dispersion axis in the input plane of said spectrometer, the sum of the diameters of all of the fibres is preferably less than or equal to the size of the detector in the non-dispersive direction divided by the magnification of the spectrometer in the non-dispersive direction. Each optical fibre constituting the optical fibre bundle is selected so that:
the diameter of the beam coming from the previous optical component at the input of the fibre is less than or equal to 120%, preferably 100%, of the useful diameter of the optical fibre, and the maximum input angle of the beam coming from the previous optical component is less than or equal to 120%, preferably 100%, of the limit angle of incidence of said optical fibre.

Thus, this construction ensures that whatever the offset of the last optical component on any axis of space, at least one optical fibre is positioned to receive all of the radiation, or almost all of the radiation. Furthermore, as the fibre bundle is oriented perpendicular to the non-dispersive direction of the spectrometer, the spectral resolution will depend on the width of the fibres and not on the diameter of the beam, although the intensity collected depends on the sum of the areas of the illuminated fibres. Such a system is particularly effective for correcting the so-called dynamic errors due to misalignments cased for example by a scanning of the sample with the charged particle beam or systematic alignment errors.

In a particular embodiment, the fibre bundle can be compact and preferably have a hexagonal input.

The diameter of each of the fibres in the fibre bundle can be identical.

Moreover, in a preferred but non-limitative version, the ratio between the total diameter of the fibre bundle and the diameter of a fibre can be between 3 and 30.

Advantageously, the first optical component can comprise a collection component that can be either a curved mirror or a plane mirror combined with a lens to collect the light radiation coming from the sample. To be inserted into the pole piece of the microscope into which the cathodoluminescence system is inserted and which enables the formation of the charged particle beam, and given that the space inside such pole pieces is smaller the better the desired spatial resolution, this collection component advantageously has a total thickness of between 0.5 and 10 mm, and preferably between 1 and 8 mm, to allow for the collection of the light radiation coming from the sample at the largest possible solid angle.

To improve the collection of the light radiation coming from the sample, the first optical component performing the collection of the light radiation can advantageously have:
- a parameter "p" of between 0.5 and 20 mm, more preferably between 1 and 7 mm, and even more preferably between 1.5 and 5 mm, still more preferably between 1 and 3 mm, or a parameter "p" of the order of 2 mm±1.5 mm; or
- a focal length "f" of between 0.25 and 10 mm, more preferably between 0.5 and 3.5 mm, and still more preferably between 0.75 and 2.5 mm.

According to an advantageous embodiment, the optical components of the optical path can be positioned so that the accuracy of the movement in at least one of the two directions of space perpendicular to the optical axis is better than or equal to:
- the size at the spectrometer input, i.e. the dimension of the pixel of the detector divided by the magnification of the spectrometer, divided by the total magnification produced on the optical path between the source and the spectrometer input, or
- when the optical component before the spectrometer is a fibre or an optical fibre bundle, the diameter of the optical fibre, or of the largest fibre in the bundle, divided by the total magnification produced on the optical path up to the input of the optical fibre or optical fibre bundle.

In such a system, the alignment accuracy in the plane perpendicular to the optical axis is such that the residual misalignments do not essentially reduce the performance described (conservation of intensity collected up to the detector, optimum spectral resolution).

Advantageously, the optical components of the optical path can also be positioned so that the accuracy in the direction of the optical axis is greater than or equal to:
- the size of the spectrometer input, i.e. the dimension of the pixel of the detector divided by the magnification of the spectrometer, divided by the magnification produced on the optical path between the source and the spectrometer input plane and by the maximum acceptance angle of the first optical component, or
- when the last optical component is a fibre or an optical fibre bundle, the diameter of the optical fibre, or the diameter of the largest fibre in the bundle, divided by the magnification produced on the optical path between the source and the input plane of the optical fibre or fibre bundle and by the maximum acceptance angle of the first optical component.

In such a system, the alignment accuracy along the optical axis is such that the residual misalignments do not essentially reduce the performance described: conservation of the intensity collected up to the detector, optimum spectral resolution, etc.

In the system according to the invention, the optical path comprises at least two optical components, at least one first optical component, called collection optic, to collect light radiation coming from the illuminated sample and at least one second optical component, called adjustment optic, to convey the radiation collected to analysis means.

This system can also comprise translation means, to translate the collection optic linearly and independently on three different axes in space. Thus, the movement of the collection optic takes place along each axis independently of the other axes. Moreover, the movement on each axis is a translation.

In a particular version of the system according to the invention, all or part of the adjustment optic can be arranged in an environment in which the pressure is greater than the pressure in a vacuum chamber in which the collection optic is arranged.

Of course the two aspects of the present invention set out above are independent of each other, but can be combined in a single cathodoluminescence system. The invention also relates to such a cathodoluminescence system combining the two aspects described in the present application.

The invention also proposes a microscope comprising:
- a source of emission of a charged particle beam, and
- a cathodoluminescence detection system according to the invention.

Advantageously, the microscope according to the invention can also comprise at least:
- one bright field detector,
- one dark field detector,
- one EELS detector,
- one camera for imaging or diffraction, or
- one EDX detector.

BRIEF DESCRIPTION OF THE DRAWINGS

Other advantages and characteristics of the invention will become apparent on examination of the detailed description of an embodiment which is in no way limitative, and the attached diagrams, in which:

FIGS. 10 and 11 are diagrammatic representations of different views of a third example of the optical path of a cathodoluminescence system according to the third aspect of the invention comprising an optical fibre bundle; and FIGS. 12 and 13 are diagrammatic representations of two configurations in which the light radiation reaches the input of the optical fibre bundle in two different positions in the system of FIGS. 10 and 11.

DETAILED DESCRIPTION

Figure 1:
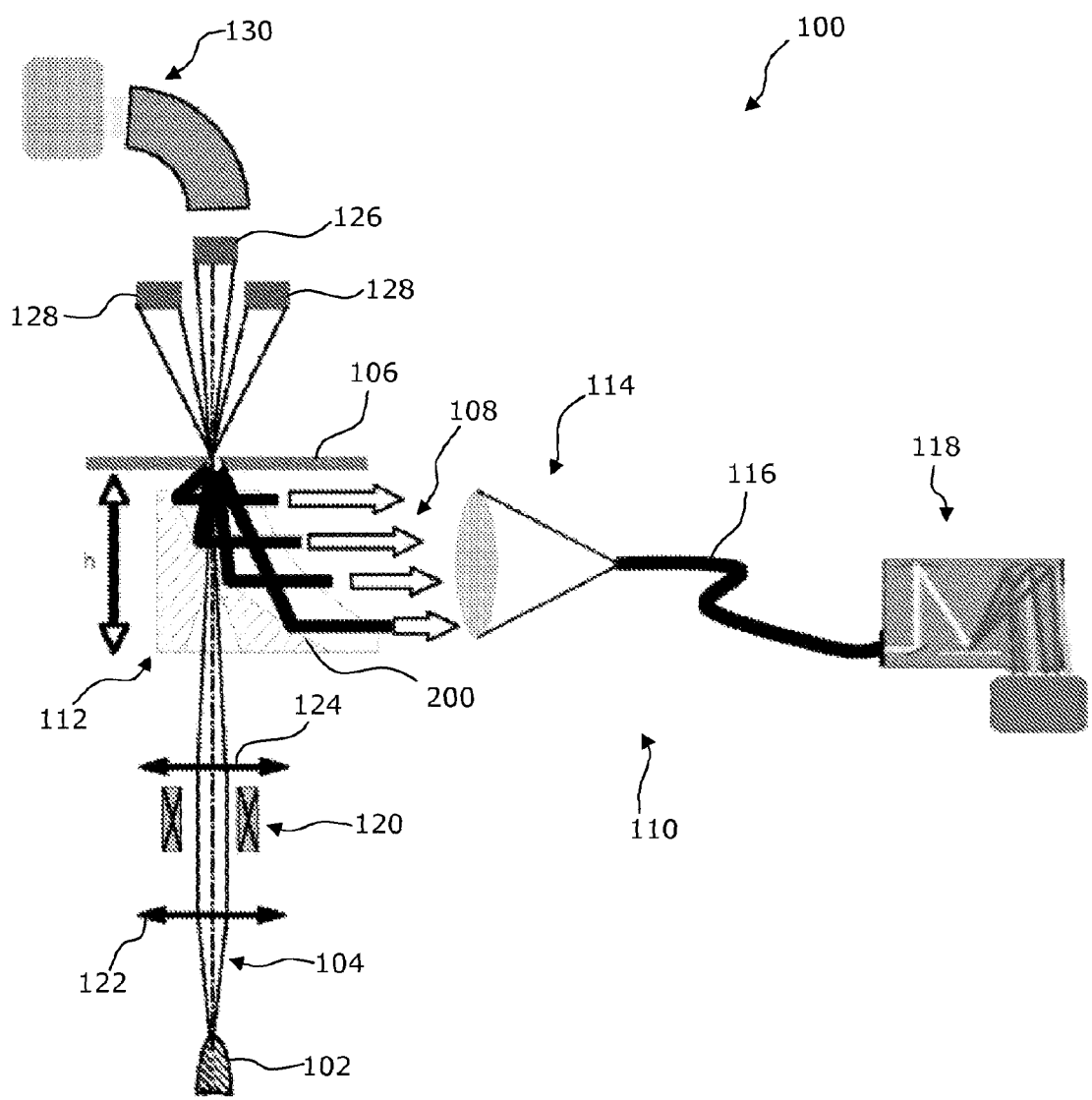
FIG. 1 is a diagrammatic representation of the principle of a microscope according to the invention implementing a cathodoluminescence detection system according to the invention.

FIG. 1 is a diagrammatic representation of the principle of the cathodoluminescence detection system implemented by a microscope 100.

The microscope 100 comprises a source 102 of emission of an electron beam 104 onto a sample 106. In response to this electron beam 104, the sample 106 emits light radiation 108 that can comprise wavelengths ranging from infrared to ultraviolet.

The light radiation 108 is then collected and analysed by a cathodoluminescence detection system 110.

The cathodoluminescence detection system 110 comprises a collection optic 112, means 114 of adjusting the diameter (respectively the angle) of the light beam 108 to the diameter (respectively numerical aperture) of an optical fibre 116 and analysis means 118. The role of the collection optic 112 is to collect the light radiation 108 emitted by the sample 106, the role of the optical fibre 116 is to convey the light radiation 108 collected by the collection optic 112 to the analysis means 118. However, it is necessary to use adjustment means 114 to adjust the light radiation 108 at the output of the collection optic 112 to the input of the optical fibre 116 while preserving the intensity and spectral resolution of the signal.

The analysis means 118 can comprise a spectrometer, a CCD camera or a photomultiplier capable of analysing the light radiation 108 conveyed by the optical fibre 116.

The microscope 100 also comprises a deflection/scanning coil 120 arranged between a condenser lens 122 positioned on the side of the electron source 102 and an objective lens 124 positioned on the opposite side. The deflection coil 120 allows for the surface of the sample 106 to be scanned with the electron beam 104 to perform a spectroscopic examination of the sample 106.

The microscope can also comprise one or more bright field detectors 126, one or more dark field detectors 128 and an EELS detector 130.

Figure 2:
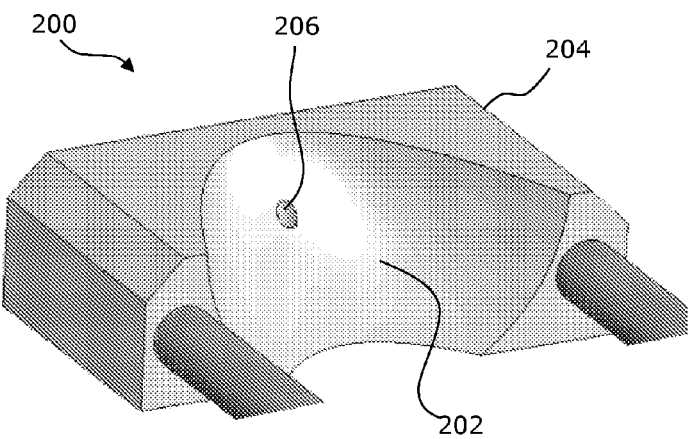
FIG. 2 is a diagrammatic representation of an example of a collection optic implemented in the cathodoluminescence system according to the invention.

In the example shown in FIG. 1, the collection optic 112 comprises a parabolic mirror 200 as shown in FIG. 2. The parabolic mirror has a reflective parabolic surface 202 cut into a block 204. The parabolic mirror 200 comprises a through-hole 206. This hole 206 is arranged opposite the electron beam 104 emission source 102. The electron beam 104 passes through this hole 206 to reach the sample 106. The light radiation emitted by the sample is then collected by the parabolic surface 202. The precise positioning of the hole 206 opposite the emission source is very important to optimise the radiance/brilliance and resolution of the light radiation collected by the parabolic surface 204.

In another embodiment (not shown), the collection optic 112 can comprise a plane mirror combined with a collecting lens or an elliptical mirror optionally combined with a collecting lens instead of the parabolic mirror.

First Aspect of the Invention

A first aspect of the cathodoluminescence system to which the present invention relates will now be described with reference to FIGS. 3-5.

Figure 3:
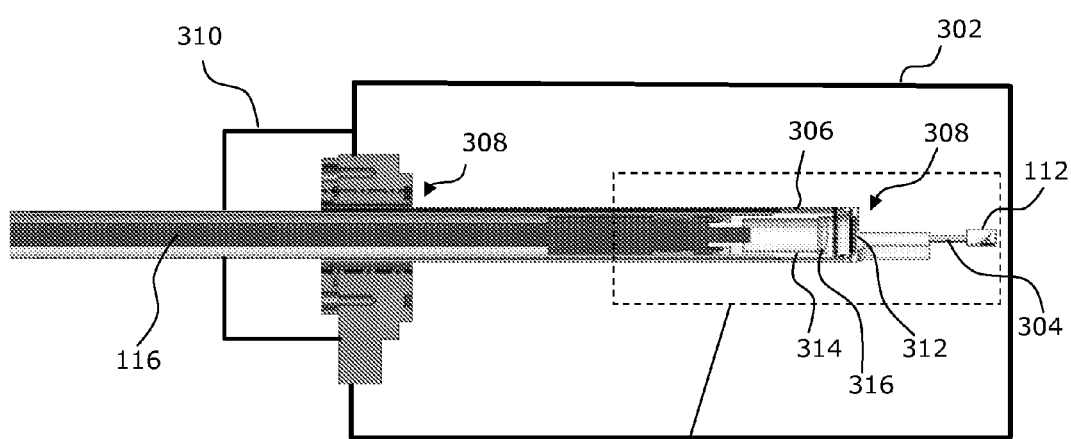
FIGS. 3 to 5 are diagrammatic representations of a first aspect of the cathodoluminescence detection system implemented by the microscope in FIG. 1.

FIG. 3 is a partial representation of the collection system relative to the vacuum chamber of a microscope.

Figure 4:
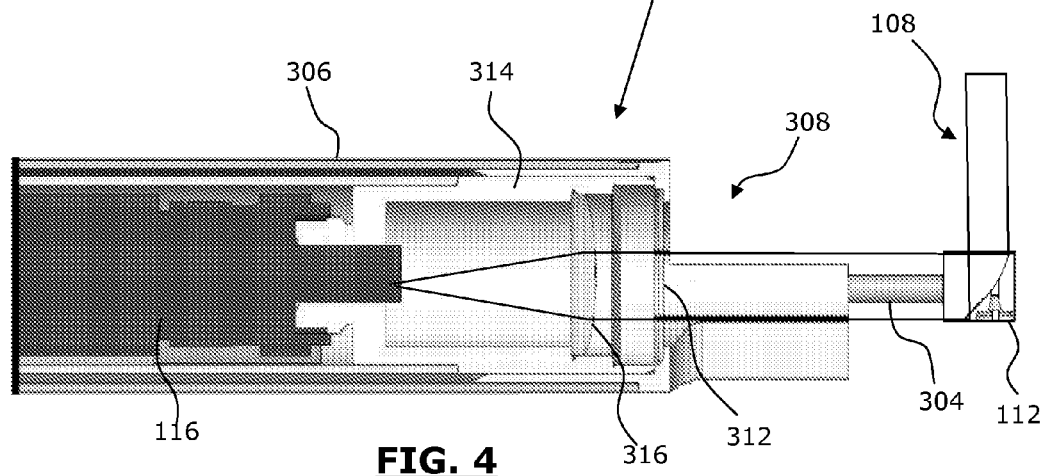
Figure 5:
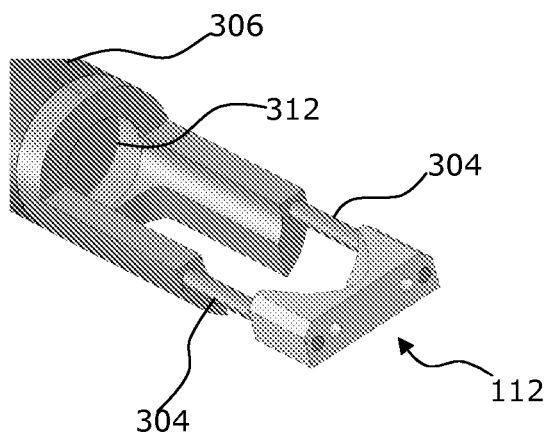

FIG. 4 is a more detailed cross-sectional representation of an area of FIG. 3 and FIG. 5 is an isometric view of the same region.

According to this first aspect, the collection optic 112 is capable of being arranged in a vacuum chamber 302 of the microscope and the adjustment means 114 as well as the optical fibre 116 and the analysis means 118 are arranged in an environment at atmospheric pressure. In other words, the adjustment means 114, the optical fibre and the analysis means are outside the vacuum chamber 302 of the microscope.

To this end, in the example shown in FIGS. 3 to 5, the collection optic 112, which is a parabolic mirror as shown in FIG. 2, is securely attached using two screws 304 to a first cylinder 306, called outer cylinder, at its proximal end 308. The collection optic 112 is connected to the outer cylinder so that the optical axis of the collection optic 112 merges with the axis of symmetry of the outer cylinder 306.

This outer cylinder 306 enters the vacuum chamber by means of an opening 308 formed in a wall of the vacuum chamber. This opening 308 is arranged opposite the light radiation sent by the collection optic 112.

The outer cylinder 306 and the wall of the vacuum chamber 302 are held together by a leaktight device 310 preserving the pressure level inside the vacuum chamber.

The outer cylinder 306 comprises at its proximal end 308, i.e. the end to which the collection optic 112 is securely attached, a transparent window seal 312 preserving the vacuum level inside the vacuum chamber 302 while letting through the light radiation collected and sent by the collection optic 112. Thus, downstream of the window seal, the inside of the outer cylinder 306 is separated from the vacuum chamber in a leaktight manner and is at atmospheric pressure.

A second cylinder 314, called inner cylinder, is arranged inside the outer cylinder 306 downstream of the window seal 312, i.e. in the part at atmospheric pressure. The axis of symmetry of the inner cylinder 314 merges with the axis of symmetry of the outer cylinder 306 and is therefore perfectly aligned with the optical axis of the collection optic 112. The inner cylinder 314 is removably arranged in the outer cylinder 306 and can rotate freely.

The adjustment means 114 are arranged in this inner cylinder 314. In the present example, shown in FIGS. 3 and 4, the adjustment means 114 comprise a convex collecting lens 316 arranged at the proximal end of the inner cylinder 314. This lens 316 allows for the width of the light radiation 108 to be adjusted at the input of the optical fibre 116.

The input of the optical fibre is also arranged inside the inner cylinder downstream of the collecting lens 316 and centred very accurately relative to the optical axis of the collecting lens 316.

The inner cylinder can also comprise any optical component necessary for the examination of the sample, for example a polariser.

The fact that the inner cylinder can rotate freely allows for the orientation of the various optical components to be modified without having to remove them.

Thus, according to this first aspect of the cathodoluminescence detection system, the optical components comprising the adjustment means and the input of the optical fibre can be accessed easily to change, repair or reposition them.

Second Aspect of the Invention

A second aspect of the cathodoluminescence system to which the present invention relates will now be described with reference to FIGS. 6 and 7.

Figure 6:
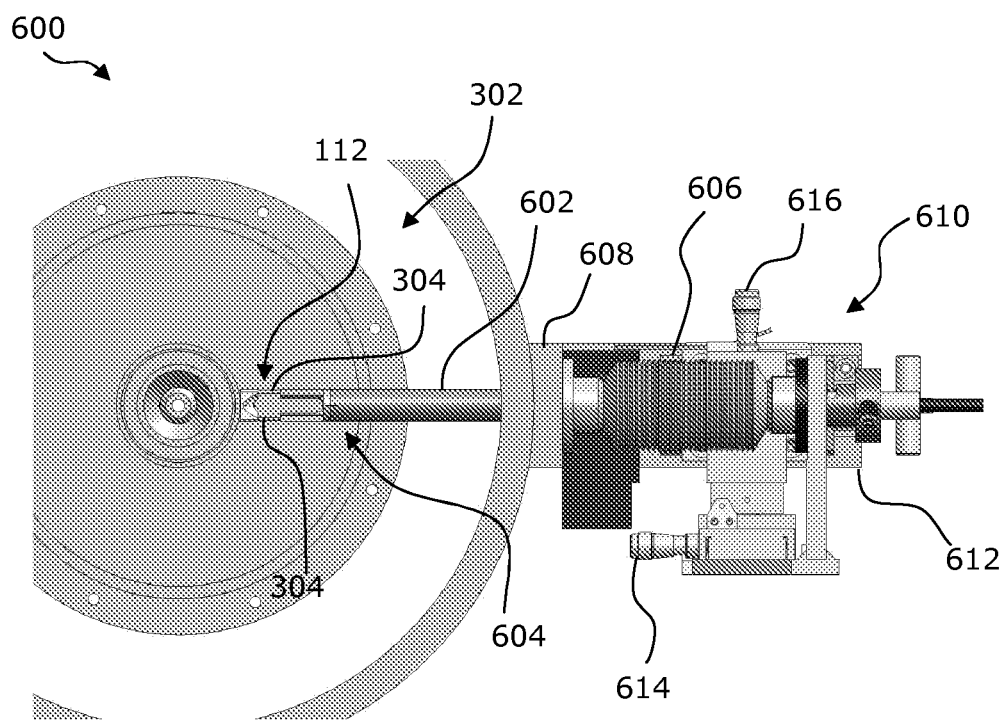
FIGS. 6 and 7 are diagrammatic representations of a second aspect of the cathodoluminescence detection system implemented by the microscope in FIG. 1.

FIG. 6 is a partial top view of a microscope 600 implementing a cathodoluminescence detection system according to the second aspect of the invention. In FIG. 6, the collection optic is completely retracted, allowing for standard use of the microscope. It is not a view of the cathodoluminescence detection system in operation. FIG. 7 is a side view of the microscope in FIG. 6.

The collection optic 112 is securely connected to a cylinder 602 by means of two screws 304 at the proximal end 604 of the cylinder 602. The collection optic 112 is located in the vacuum chamber 302 of the microscope 600. The cylinder 602 can also comprise optical adjustment means 114 and the input of the optical fibre 116, which can for example be arranged in a second cylinder removably inserted into the cylinder 602, rotating freely and mounted so that the axis of symmetry merges with the axis of symmetry of the cylinder 602. The cylinder 602 can be the outer cylinder 306 and comprise the inner cylinder 314, as described above.

The cylinder 602 enters the vacuum chamber 302 by means of an opening 604 formed in a wall of the vacuum chamber. This opening 604 is arranged opposite the light radiation sent by the collection optic 112. The diameter of this opening is greater than the outer diameter of the cylinder 602 in order to allow the movement of the outer cylinder in the three dimensions of space. This opening 604 can be the opening 308 described above.

A bellows seal 606 is attached to the cylinder 602 and surrounds the cylinder 602 in a leaktight manner. This bellows seal is moreover attached in a leaktight manner to the wall of the vacuum chamber 302, around the opening 602, by means of a connecting part 608 that hugs the outer shape of the wall of the vacuum chamber around the opening 602. Thus, the connection between the bellows seal 606 and the cylinder 602 is leaktight, as is the connection between the bellows seal 606 and the wall of the vacuum chamber 302. The bellows seal 606 permits the movement of the cylinder 606 in the three directions of space while at all times preserving the leaktightness of each of its connections with the cylinder 602 on the one hand and the wall of the vacuum chamber 302 on the other hand.

Figure 7:
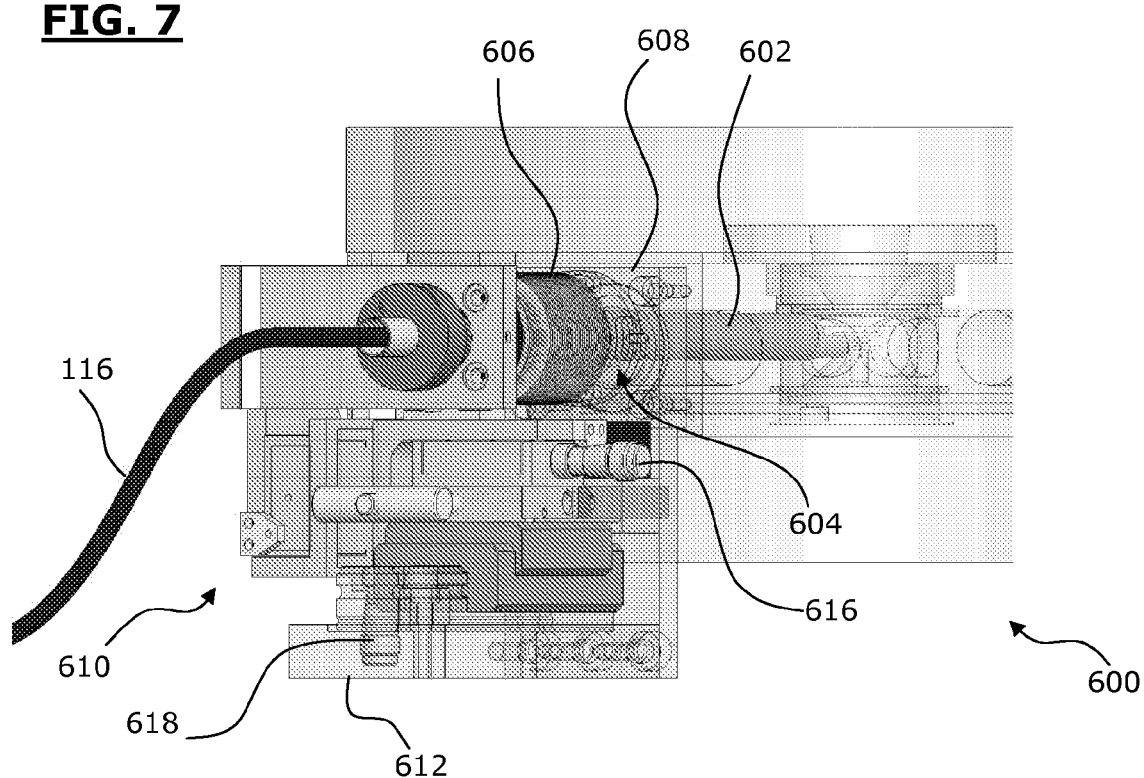

The cylinder 602 comprises a window seal (not shown in FIGS. 6-7). This window seal allows for the leaktightness of the vacuum chamber 302 to be preserved. This window seal can be arranged upstream or downstream of the optical adjustment means 114 and the input of the optical fibre 116. This window seal can for example be the window seal 312 in FIGS. 3-5, when the two aspects of the cathodoluminescence system described in the present application are combined.

The cylinder 602 is securely mounted on a three-dimensional movement device 610 on the side of its distal end 612, i.e. the end on the opposite side to the collection optic 112. This three-dimensional movement device 610 is placed on a stage 612 movably mounted on the wall of the vacuum chamber 302. The device 610 comprises three micrometric screws 614, 616 and 618 used to move the cylinder 602 in the three dimensions of space.

As the collection optic 112 is integral with the cylinder 602, the movement of the cylinder 602 results in the movement of the collection optic 112. Thus, by means of this second aspect of the cathodoluminescence detection system, it is possible for the operator to move the collection optic from the outside of the microscope to position it better in relation to the electron emission source and relative to the sample, to improve the conservation of the intensity of the light radiation collected downstream of the collection optic, together with the spectral resolution of the optical signal.

On reading the present application, it is clear to a person skilled in the art that the first and second aspects of the cathodoluminescence detection system can be combined. As set out above, the cylinder 602 shown in FIGS. 6 and 7 can be replaced by the outer cylinder 306 in FIGS. 3 to 5 comprising the window seal 312, the inner cylinder 314 in which the adjustment means 114 (in particular the collecting lens 316) are arranged, and the input of the optical fibre 116. By combining the first and second aspects of the invention it is possible to obtain a cathodoluminescence detection system that is both flexible and adjustable and can be used to optimise the light intensity collected and its conveyance to the analysis means while conserving optimum spectral resolution by common, easy-to-implement means.

Third Aspect of the Invention

Figure 8:
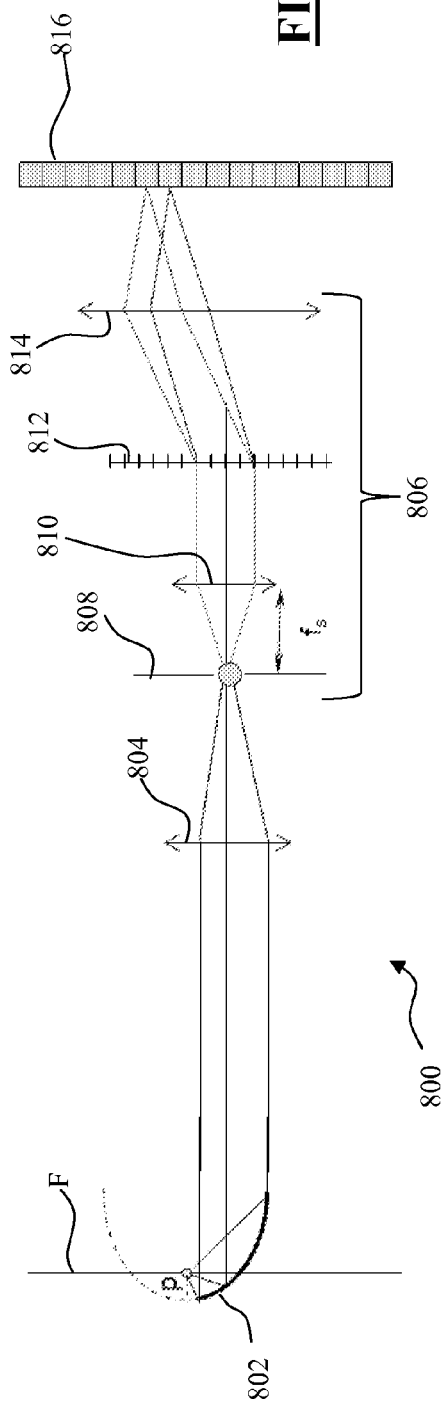
FIG. 8 is a diagrammatic representation of a first example of the optical path of a cathodoluminescence system according to a third aspect of the invention.

FIG. 8 is a diagrammatic representation of a first example of the optical path of a cathodoluminescence system according to the third aspect of the invention.

The optical path 800 in FIG. 8 comprises as a means of collection a parabolic mirror 802 that can be identical to the parabolic mirror 200 in FIG. 2, which collects light radiation coming from a sample illuminated by a particle beam.

The optical path 800 comprises as processing means a lens 804, which can be the lens 316 in FIGS. 3 and 4, receiving the light radiation collected by the parabolic mirror 802 and injecting it into a spectrometer 806 the input of which is represented by the plane 808. The spectrometer 806 comprises a lens 810 arranged upstream of the grating 812 of the spectrometer 806 which sends the light radiation entering the spectrometer 806 to the grating 812 of the spectrometer 806. The spectrometer 806 also comprises a lens 814 arranged downstream of the grating 812 of the spectrometer 806 that represents the output of the spectrometer and sends the light radiation leaving the spectrometer 806 to a CCD camera 816. The spectrometer 806 and the camera 816 constitute the analysis means of the cathodoluminescence system.

According to the third aspect of the invention, the parabolic mirror, the lens 804 and the spectrometer 806 are selected and positioned so that:

the parabolic mirror 802 has a value of p of 2 mm and a thickness of 3 mm;

the maximum output angle of the parabolic mirror 802 is zero (parallel beam) and the maximum input angle of the lens 804 is zero (parallel beam);

the profile of the radiation coming from the parabolic mirror 802 in the input plane of the lens 804 is 9 mm by 3 mm and the useful input diameter of the lens 802 is 8 mm;

taking the centre of the parabolic mirror to be the mid-point between its horizontal and vertical surfaces (parallel to the optical axis of the lens), the offset of the lens 804 relative to the centre of the parabolic mirror is less than 100 microns. The position of the focus of the mirror is under these circumstances calculated to obtain the maximum collection angle for the mirror; and the maximum output angle of the lens 804 is 6.3°.

Moreover:

the width of the beam at the input of said spectrometer in the dispersive direction is typically 100 or 70 microns and the limit diameter at the input of the spectrometer below which the resolution of the spectrometer no longer depends on the diameter of the waist of the light radiation at the input of the spectrometer is 70 μm.

Moreover:

the accuracy of the movement in at least one of the two directions of space perpendicular to the optical axis and in the direction of the optical axis is greater than or equal to 1 μm, ensuring resolution at the input of the spectrometer better than 30 microns, i.e. less than the limit size at the input of the spectrometer below which resolution deteriorates.

Figure 9:
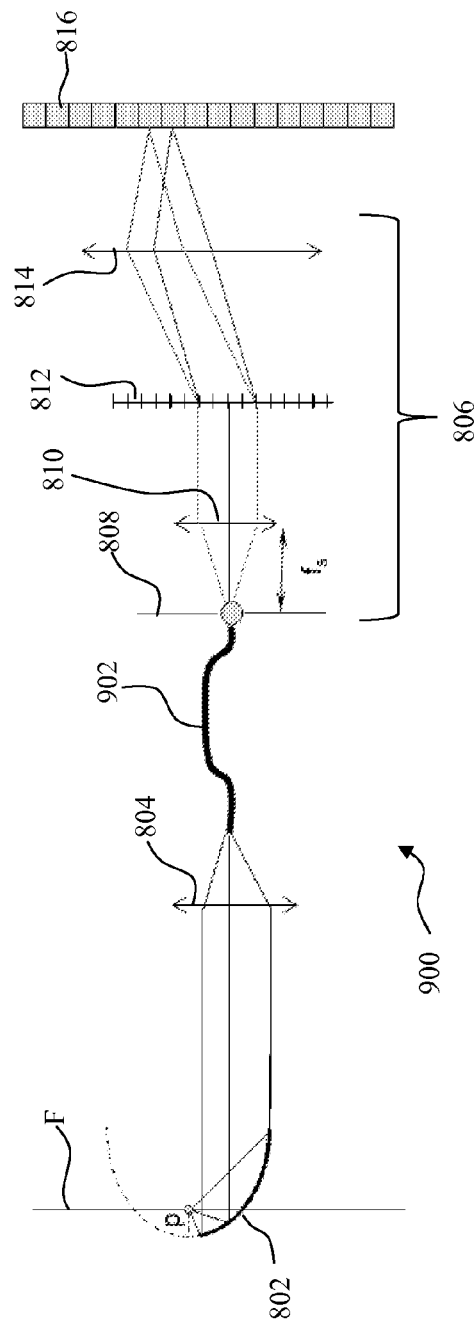
FIG. 9 is a diagrammatic representation of a second example of the optical path of a cathodoluminescence system according to a third aspect of the invention comprising an optical fibre.

FIG. 9 is a diagrammatic representation of a second example of the optical path of a cathodoluminescence system according to the third aspect of the invention.

The optical path 900 in FIG. 9 comprises all of the components of the optical path 800 shown in FIG. 8.

The optical path 900 also comprises an optical fibre 902, which can be the optical fibre 116 in FIGS. 3 and 4. The input of the optical fibre 902 is positioned at the focal point of the lens 804 and the output of the optical fibre is positioned in the input plane of the spectrometer 806 represented by the plane 808.

The parameters of the optical components of the optical path 900 are identical to the parameters given with reference to FIG. 1.

However:

the width of the radiation at the input of the optical fibre 902 is, if the object being examined is infinitely small, of the order of 15 microns, and the useful input diameter of the optical fibre is 70 μm;

the maximum angle of the radiation coming from the lens 804 is 6.3° and the limit angle of incidence at the input of the optical fibre 902 is 6.9°; and the offset of the fibre 902 relative to the centre of the lens is less than 100 microns.

Moreover:

the width of the beam at the input of said spectrometer in the dispersive direction is 70 μm and the limit diameter at the input of the spectrometer below which the resolution of the spectrometer no longer depends on the diameter of the waist of the light radiation at the input of the spectrometer is 70 μm.

Moreover:

the accuracy of the movement in at least one of the two directions of space perpendicular to the optical axis and in the direction of the optical axis is greater than 1 μm, ensuring resolution at the input of the optical fibre better than 30 microns, i.e. less than the limit size at the input of the spectrometer below which resolution deteriorates; and the diameter of each optical fibre divided by the magnification produced on the optical path up to the optical fibre bundle 1002 is 2 μm.

FIGS. 10 and 11 are diagrammatic representations of different views of a third example of the optical path of a cathodoluminescence system according to the third aspect of the invention comprising an optical fibre bundle.

The optical path 1000 in FIGS. 10 and 11 comprises all of the components of the optical path 800 shown in FIG. 8.

The optical path 1000 also comprises an optical fibre bundle 1002, made up for example of several optical fibres such as the optical fibre 902 in FIG. 9. The input of the optical fibre bundle 1002 is positioned at the focal point of the lens 804 and the output of the optical fibre bundle is positioned on the input plane of the spectrometer 806 represented by the plane 808.

The parameters of the optical components of the optical path 1000 are identical to the parameters given with reference to FIG. 1.

However:

the width of the radiation at the input of the optical fibre bundle 1002 is greater than or equal to 200 microns and the useful input diameter of each optical fibre constituting the optical fibre bundle 1002 is 70 μm;

the maximum input angle of the radiation coming from the lens 804 is 6.3° and the limit angle of incidence at the input of each optical fibre constituting the optical fibre bundle 1002 is 6.9°; and the offset of the optical fibre bundle 1002 relative to the centre of the lens is of the order of one hundred microns.

Moreover:

the width of the beam at the input of said spectrometer in the dispersive direction is 70 μm and the limit diameter at the input of the spectrometer below which the resolution of the spectrometer no longer depends on the diameter of the waist of the light radiation at the input of the spectrometer is 70 μm.

Moreover:

the accuracy of the movement in at least one of the two directions of space perpendicular to the optical axis and in the direction of the optical axis is 1 μm or better than 1 μm, ensuring resolution at the input of the optical fibre better than 30 microns, i.e. less than the limit waist at the input of the spectrometer below which resolution deteriorates; and the diameter of each optical fibre divided by the magnification produced on the optical path up to the optical fibre bundle 1002 is 2 μm.

According to the invention, each of these three embodiments allows for the light radiation emitted by the sample to be conveyed to the CCD camera while preserving more light intensity, optimum spectral resolution and the possibility of using the invention in a microscope using charged particles capable of forming nanometric or even angstromic probe beams.

Moreover, the third example shown in FIGS. 10 and 11 also allows for the correction of dynamic or systematic errors or errors due to scanning of the sample.

To this end, at the input 1202 of the bundle 1002, the optical fibres constituting the bundle 1002 are arranged in a circular or hexagonal manner around each other. At the output 1204 of the bundle 1002, the optical fibres constituting the bundle 1002 are aligned on top of each other in a direction perpendicular to the dispersive direction of the spectrometer. The input 1202 and the output 1204 of the optical fibre bundle 1002 are shown diagrammatically in FIGS. 12 and 13.

FIGS. 12 and 13 are diagrammatic representations of two configurations in which the light radiation reaches the input of the optical fibre bundle in two different positions in the system in FIGS. 10 and 11. In the configuration shown in FIG. 12, the light radiation reaches the input 1202 of the optical fibre bundle 1002 at a point 1206 offset to the left relative to its centre and in the configuration shown in FIG. 13, the light radiation reaches the input 1202 of the optical fibre bundle 1002 at a point 1302 offset to the right relative to its centre. Depending on the fibres concerned, the light radiation entering the optical fibre bundle 1002 does not leave the optical fibre bundle 1002 in the same positions. However, in both cases and despite the difference in position of the light radiation reaching the input plane of the optical fibre bundle 1002, all of the radiation is collected and conveyed to the spectrometer by the optical fibre bundle 1002 and the spectra 1208 and 1304 obtained at the CCD camera for each of the two sets of radiation are identical. This takes place without any loss of spectral resolution or intensity.

The three aspects of the present invention can be combined, in twos or all three, in a single cathodoluminescence system.

Of course, the invention is not limited to the examples which have just been described and numerous adjustments can be made to these examples without exceeding the scope of the invention.

The invention claimed is:

1. A cathodoluminescence detection system comprising:
a source of charged particles arranged to illuminate a sample with a charged particle beam, and
an optical path comprising at least two optical components capable of collecting and conveying light radiation coming from said illuminated sample to analysis means, a first optical component of said at least two optical components is a collection component to collect light emitted from the sample, and a second optical component of said at least two optical components is downstream from the collection component in the direction of the light emitted from the sample,
each optical component of said optical path is selected so that:
the maximum output angle of said optical component is less than or equal to 120% of the maximum acceptance angle of the next optical component; and
the diameter of the radiation coming from said optical component in the input plane of the next optical component is less than or equal to 120% of the useful input diameter of the next optical component.

2. The system according to claim 1, wherein each optical component on the optical path is selected so that the maximum output angle of an optical component is less than or equal to the maximum acceptance angle of the next optical component.

3. The system according to claim 1, wherein each optical component of the optical path is selected so that the diameter of the radiation coming from an optical component in the input plane of the next optical component is less than or equal to the useful input diameter of the next optical component.

4. The system according to claim 1, wherein each optical component of the optical path is positioned so that the offset of one optical component relative to the centre of the previous optical component complies with the following relationship:

$$Ds_i/2 \leq 1.2 De_{i+1}/2 - \Delta_{i+1} \text{ for } i=1 \ldots N-1$$

where:
N is the total number of the optical components in the optical path
$\Delta_{i+1}$ is the offset of optical component $i+1$ relative to the centre of optical component i,
$De_{i+1}$ is the useful input diameter of component $i+1$,
$Ds_i$ is the diameter of the radiation coming from component i measured at the input of component $i+1$.

5. The system according to claim 4, wherein each optical component of the optical path is positioned so that the offset of one optical component relative to the center of the previous optical component verifies the following equation:

$$Ds_i/2 \leq De_{i+1}/2 - \Delta_{i+1} \text{ for } i=1 \ldots N-1.$$

6. The system according to claim 1, wherein at least one of the optical components on the optical path is a spectrometer comprising a focusing component at its input, said spectrometer and the other optical components of the optical path being selected so that the width of the beam at the input of the spectrometer in the dispersive direction is less than or equal to the limit diameter at the input of the spectrometer below which the resolution of the spectrometer no longer depends on the diameter of the waist of the light radiation at the input of the spectrometer.

7. The system according to claim 6, wherein the optical component before the spectrometer comprises an optical fiber the output of which is positioned or imaged at the input of the spectrometer, said optical fiber and the optical component before the optical fiber are selected so that:
the diameter of the beam coming from the previous optical component measured at the input of the optical fiber is less than or equal to 100% of the useful diameter of the optical fiber, and
the maximum input angle of the beam coming from the previous optical component is less than or equal to 100% of the limit angle of incidence of said optical fiber.

8. The system according to claim 6, wherein the optical component before the spectrometer comprises a plurality of optical fibers constituting an optical fiber bundle:
the optical fibers of said bundle being aligned, on the side of said spectrometer, perpendicular to the dispersion axis in the input plane of said spectrometer, and
the sum of the diameters of all of the optical fibers is preferably less than or equal to the size of the detector of the spectrometer in the non-dispersive direction divided by the magnification of the spectrometer in the non-dispersive direction; and
each optical fiber constituting the optical fiber bundle is selected so that:
the diameter of the beam coming from the previous optical component at the input of the optical fiber is less than or equal 100% of the useful diameter of the optical fiber, and
the maximum input angle of the beam coming from the previous optical component at the input of the optical fiber is less than or equal to 100% of the limit angle of incidence of said optical fiber.

9. The system according to claim 1, wherein the optical component before the spectrometer comprises a plurality of optical fibers constituting an optical fiber bundle:
the optical fiber bundle is compact and has a hexagonal input, and/or
the ratio between the total diameter of the optical fiber bundle and the diameter of an optical fiber is between 3 and 30.

10. The system according to claim 1, wherein the collection component has a total thickness of between 1 and 8 mm.

11. The system according to claim 10, wherein the collection component performing the collection of the light radiation has:
if it is a paraboloid, a parameter "p" of between 1 and 3 mm, or a parameter "p" of the order of 2 mm ±1.5 mm; or
focal length "f" of between 0.75 and 2.5 mm.

12. The system according to claim 1, wherein the optical components of the optical path are capable of being positioned in two dimensions of space perpendicular to the optical axis, such that, when the optical path comprises a spectrometer, the accuracy of the movement in at least one of the two directions is greater than or equal to:
the size at the spectrometer input, i.e. the dimension of the pixel of the detector divided by the magnification of the spectrometer, divided by the total magnification produced on the optical path between the source and the spectrometer input, or when the optical component before the spectrometer is an optical fiber or an optical fiber bundle, the diameter of the optical fiber, or of the largest optical fiber in the bundle, divided by the total magnification produced on the optical path up to the input of the optical fiber or optical fiber bundle.

13. The system according to the claim 12, wherein the accuracy of the displacement of an optical component in at least one direction is greater than or equal to:

the size of the spectrometer input, i.e. the dimension of the pixel of the detector divided by the magnification of the spectrometer, divided by the magnification produced on the optical path between the source and the spectrometer input plane and by the maximum acceptance angle of the first optical component, or when a last optical component is an optical fiber or an optical fiber bundle, the diameter of the optical fiber, or the diameter of the largest optical fiber in the bundle, divided by the magnification produced on the optical path between the source and the input plane of the optical fiber or optical fiber bundle and by the maximum acceptance angle of the first optical component.

14. A microscope comprising:

a source of emission of a charged particle beam, and a cathodoluminescence detection system according to claim 1.

15. The microscope according to claim 14, further comprising at least one of:

one bright field detector;

one dark field detector one Electron Energy Loss Spectroscopy (EELS) detector;

one camera for imaging or diffraction; and one Energy-Dispersive X-ray Spectroscopy (EDX) detector.

* * * * *

UNITED STATES PATENT AND TRADEMARK OFFICE
CERTIFICATE OF CORRECTION

PATENT NO. : 9,228,962 B2
APPLICATION NO. : 14/540220
DATED : January 5, 2016
INVENTOR(S) : Mathieu Kociak et al.

Page 1 of 1

It is certified that error appears in the above-identified patent and that said Letters Patent is hereby corrected as shown below:

Title page item (73) Assignees, delete "Centre National de la Recherche, Paris (FR)" and please insert
-- Centre National de la Recherche Scientifique, Paris (FR)" --.

Signed and Sealed this
Sixteenth Day of August, 2016

Michelle K. Lee
*Director of the United States Patent and Trademark Office*